United States Patent [19]

Alexander

[11] Patent Number: 5,053,387
[45] Date of Patent: Oct. 1, 1991

[54] OMEGA-3 FATTY ACIDS IN TRAUMATIC INJURY TREATMENT

[75] Inventor: J. Wesley Alexander, Cincinnati, Ohio

[73] Assignee: Shriners Hospitals for Crippled Children

[21] Appl. No.: 524,667

[22] Filed: May 16, 1990

Related U.S. Application Data

[63] Continuation of Ser. No. 418,690, Oct. 2, 1989, abandoned, which is a continuation of Ser. No. 298,825, Jan. 18, 1989, abandoned, which is a continuation of Ser. No. 17,326, Feb. 20, 1987, abandoned, which is a continuation-in-part of Ser. No. 2,035, Jan. 12, 1987, abandoned.

[51] Int. Cl.$^5$ ............ A61K 37/02; A61K 31/70; A61K 35/60; A61K 31/20
[52] U.S. Cl. .................... 514/2; 514/21; 514/23; 514/54; 514/396; 514/560; 514/561; 514/562; 514/867; 424/523; 424/DIG. 13
[58] Field of Search ............... 514/2, 21, 23, 54, 396, 514/560, 561, 562, 867; 424/523, DIG. 13; 530/833

[56] References Cited

U.S. PATENT DOCUMENTS 4,401,657  8/1983  Kashiwabara et al. ............... 514/21
4,678,808  7/1987  Ward et al. ........................... 514/560

FOREIGN PATENT DOCUMENTS 1197782  12/1985  Canada ............................... 514/560

OTHER PUBLICATIONS

Mochizuki et al., JPEN, vol. 8, No. 6, (1984), pp. 638–646.
Gottschlich et al.: Fat Kinetics and Recommended Dietary Intake in Burns, Journal of Parenteral and Enteral Nutrition 11, 1:80–85, 1987.
Alexander, J. W.: Nutrition and Infection, Arch. Surg. 121:966–972, 1986.
Alexander, J. W. et al.: The Importance of Lipid Type in the Diet After Burn Injury, Annals of Surgery 204, 1:1–8, 1986.
Dominioni, L. et al.: Enteral Feeding in Burn Hypermetabolism; Nutritional and Metabolic Effects of Different Levels of Calorie and Protein Intake, Journal of Parenteral and Enteral Nutrition 9, 3:269–279, 1985.
Alexander, J. W.: Burn Care: Specialty in Evolution—1985 Presidential Address, American Burn Association, The Journal of Trauma 26, 1:1–6, 1986.
Trocki, O. et al.: Comparison of Continuous and Intermittent Tube Feedings in Burned Animals, JBCR 7, 2:130–137, 1986.
Trocki, O. et al.: Intact Protein Versus Free Amino Acids in the Nutritional Support of Thermally Injured Animals, Journal of Parenteral and Enteral Nutrition 10, 2:139–145, 1986.
Saito, H. et al.: The Effect of Route of Nutrient Administration on the Nutritional State, Catabolic Hormone Secretion and Gut Mucosal Integrity Following Burn Injury, submitted to JPEN, Jan. 1986.

(List continued on next page.)

Primary Examiner—Jacqueline Stone
Attorney, Agent, or Firm—Frijouf, Rust & Pyle

[57] ABSTRACT

A composition and method of treating a traumatic injury by improving immunologic response and reducing a hypermetabolic response associated with those suffering from a traumatic injury such as a substantial burn, trauma, major surgery and the like and more particularly to those suffering from a substantial thermal burn injury to the skin or other areas through the administration of the composition of the invention to those suffering from the traumatic injury are disclosed. The composition comprises an intact protein, arginine, carbohydrate, lipid comprising the omega-3 fatty acids of fish oil, including eicosapentaenoic acid, and with linoleic acid limited to the amount necessary to prevent an essential fatty acid deficiency thereof and nutritionally necessary vitamins and minerals.

10 Claims, 2 Drawing Sheets

OTHER PUBLICATIONS

Postburn Period, JPEN, 8(6), pp. 638-646, 1984 (abstract).

Oliet, M. P. et al.: Whey Protein Supplementation of Complete Tube Feeding in the Nutritional Support of Thermally Injured Patients, ABA orally presented Mar., 1983, New Orleans Meeting (abstract).

Dominioni, L. et al.: Prolonged Hypercaloric Enteral Feeding in the Guinea Pig Undergoing Severe Burn Trauma, The Effects of Different Levels of Protein Intake, XVIII Congress of the European Society for Surgical Research, Greece, 1983 (abstract).

Mochizuki, H. et al.: Effect of a Diet Rich in Branched Chain Amino Acids on Severely Burned Guinea Pigs, In Press, J. Trauma.

Mochizuki, H. et al.: Reduction of Postburn Hypermetabolism by Early and Enteral Feeding, Current Surgery, vol. 42, No. 2 (1985).

Mochizuki, H. et al.: Mechanism of Prevention of Postburn Hypermetabolism and Catabolism by Early Enteral Feeding, Annals of Surgery, vol. 200, No. 3, Sep., 1984.

Mochizuki, H. et al.: Optimal Lipid Content for Enteral Diets Following Thermal Injury, Journal of Parenteral and Enteral Nutrition 8, 6:638-646, 1984.

Dominioni, L. et al.: Gastrotomy Feeding in Normal and Hypermetabolic Burned Guinea Pigs: A Model for the Study of Enteral Diets, JBCR 5, 2:100-104, 1984.

Mochizuki, H. et al.: The Effect of Nutritional Support with Different Levels of Fat on Burned Guinea Pigs, American Burn Association, orally presented Apr., 1984, San Francisco Meeting (abstract).

Dominioni, L. et al.: Prevention of Severe Postburn Hypermetabolism and Catabolism by Immediate Intragastric Feeding, JBCR 5, 2:106-125, 1984.

Trocki, O. et al.: Intact Protein Versus Free Amino Acids in the Nutritional Support on Thermally Injured Animals, American Burn Association orally presented 1984, Orlando Meeting (abstract).

Saito, H. et al.: Metabolic and Immune Effects of Dietary Arginine Supplementation After Burn, In Press Arch. Surg.

Dominioni, L. et al.: Nitrogen Balance and Liver Changes in Burned Guinea Pigs Undergoing Prolonged High-Protein Enteral Feeding, American College of Surgeons Surgical Forum 34:99-101, 1983.

Alexander, J. W.: Optimal Fat Proportion in Diet for

OMEGA-3 FATTY ACIDS IN TRAUMATIC INJURY TREATMENT

RELATED APPLICATION

This application is a continuation of application Ser. No. 418,690, filed Oct. 2, 1989, which is a continuation of Ser. No. 298,825, filed Jan. 18, 1989, which is a continuation of Ser. No. 17,326, filed Feb. 20, 1987, which is a continuation-in-part of Ser. No. 2,035 filed Jan. 12, 1987, all now abandoned.

BACKGROUND OF THE INVENTION

1. Field of the Invention

This invention relates to a nutritionally fortified pharmaceutical composition for the administration to patients in a hypermetabolic state such as those suffering from a substantial burn, trauma, major surgery and the like, and more particularly to a composition for enteral administration to patients who have encountered a substantial burn injury to the skin or other areas from contact with heat, radiation, electricity or chemicals.

2. Disclosure Statement

Patients suffering from a traumatic injury such as a substantial burn (involving an area greater than about 45 percent of the surface area of a human) become hypermetabolic and are highly susceptible to the development of malnutrition and infection. In 1970 of the patients who survived more than one week, roughly 75 percent died of infectious complications. While substantial improvement has taken place since then, what is needed is an improved nutritionally fortified pharmaceutical composition which will aid the traumatically injured patient manifesting or about to manifest a hypermetabolic state associated with a traumatic injury by attenuating the hypermetabolic state thereby lessening malnutrition and infection associated with a traumatic injury. In patients where the GI tract is still functioning but who are unable to orally take in adequate amounts of nutrients, enteral nutrition is the preferred route of nutritional administration relative the parenteral route.

Generally speaking, enteral nutrition products may be administered orally or by tube feeding routes. The nasogastric, nasoduodenal and nasojejunol routes are nonsurgical. Whereas, the jejunostomy, gastrostomy and esophagostomy are surgically inserted. Enteral nutrition products may also be administered by mouth where the patient is able. The nasoduodenal and nasojejunal are generally used in an unconscious patient and those with an impaired gag reflex in order to minimize the likelihood of aspiration.

Numerous enteral formulations are utilized in patients with a hypermetabolic state as effected by burns, trauma, major surgery and in those patients with malnutrition syndromes, neoplasms, chronic illnesses and in disorders resulting from prolonged periods of reduced oral intake resulting from cerebral vascular accidents or a comatose state.

ISOCAL is an enteral formulation by Mead Johnson which utilizes casein and soy for its protein source, glucose oligosacchrides for its carbohydrate source and soy oil and medium chain triglycerides (MCT) oil for its lipid source. The composition includes about 19 grams linoleic acid per liter.

OSMOLITE is manufactured by Ross and utilizes as its protein source casein and soy, corn starch for its carbohydrate source and fifty percent MCT oil, forty percent corn oil and ten percent soy oil for its lipid source. The composition includes about 11.5 grams linoleic acid per liter.

ENSURE is manufactured by Ross and utilizes casein and soy for protein source, corn starch and sucrose for a carbohydrate source and corn oil for a lipid source. The composition includes about 19.6 grams linoleic acid per liter.

SUSTACAL manufactured by Mead Johnson utilizes casein and soy for its protein source, corn syrup and sucrose for its carbohydrate source and soy oil for its lipid source. The composition includes about 6.8 grams linoleic acid per liter.

ENSURE PLUS manufactured by Ross is a high protein composition using soy and casein for its protein source, corn starch and glucose for its carbohydrate source and corn oil for its lipid source. The composition includes about 27 grams linoleic acid per liter.

MAGNACAL manufactured by Chesebrough Ponds is a high density composition with 2.0 calories/ml. MAGNACAL utilizes casein for its protein source, corn syrup for its carbohydrate source and soy oil for its lipid source. The composition includes about 59 grams linoleic acid per liter.

TRAUMACAL manufactured by Mead Johnson utilizes casein for its protein source, corn syrup and sucrose for its carbohydrate source and 70 percent soy bean oil and 30 percent MCT oil for its lipid source. The composition includes about 27 grams linoleic acid per liter.

PRECISION ISOTEIN HN is manufactured by Sandoz and utilizes lactalbumin for its protein source, maltodextrin for its carbohydrate source and soy oil and MCT oil for its lipid source. The composition includes about 3.4 grams linoleic acid per liter.

The above enteral compositions fail to provide omega-3 fatty acids including eicosapentaenoic acid or a nutritionally fortified pharmaceutical composition containing omega-3 fatty acids of fish oil including eicosapentaenoic acid for the reduction or attenuation of hypermetabolic states associated with traumatic injuries such as a burn injury, trauma and major surgery and especially substantial burn injuries.

Therefore, it is an object of this invention to provide a nutritionally fortified pharmaceutical composition and method to aid in the treatment of a traumatic injury with an impaired immune response and an associated hypermetabolic state especially where the hypermetabolic state and immunologic depression are the result of a traumatic injury such as a substantial burn injury.

Another object of this invention is to provide a nutritionally fortified pharmaceutical composition which provides omega-3 fatty acids including eicosapentaenoic acid in an amount sufficient to reduce the hypermetabolic resting metabolic state associated with those suffering from a traumatic injury and limits the amount of linoleic acid in the composition to the amount needed for preventing essential fatty acid deficiency.

Another object of this invention is to provide a nutritionally fortified pharmaceutical composition for administration to one suffering from a traumatic injury which decreases the amount of arachidonic acid pathway metabolites formed in a traumatically injured patient thereby enhancing healing of a traumatic injury in the patient in need of such treatment.

Another object of this invention is to provide a method of treating a patient suffering from a traumatic injury, such as a burn injury, by providing to one in need of such treatment omega-3 fatty acids including eicosapentaenoic acid in an amount sufficient to attenuate a hypermetabolic response associated with the traumatic injury and limiting the amount of linoleic acid to the amount needed for preventing essential fatty acid deficiency to enhance the healing rate of the burn injury.

Another object of this invention is to provide a nutritionally fortified pharmaceutical composition which provides omega-3 fatty acids including eicosapentaenoic acid which enhances the healing rate of a traumatic injury.

Another object of this invention is to provide a nutritionally fortified pharmaceutical composition and method which results in less weight loss, in better skeletal muscle mass maintenance, in a lower resting metabolic expenditure, better opsonic indices, higher splenic weight, lower adrenal weight, higher serum transferrin, lower serum C3 levels and in a better cell mediated immune response for use in a patient with a traumatic injury and its associated hypermetabolic response and immunologic depression.

Another object of this invention to provide a composition which attenuates a hypermetabolic response in a patient in need of such treatment.

The foregoing has outlined some of the more pertinent objects of the present invention. These objects should be construed to be merely illustrative of some of the more pertinent features and applications of the invention. Many other beneficial results can be obtained by applying the disclosed invention is a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying formulations and figures.

SUMMARY OF THE INVENTION

The nutritionally fortified pharmaceutical composition and method of treating burns of the present invention are defined by the appended claims with a specific embodiment shown in the included formulations and figures. For purposes of summarizing the invention, the invention relates to a composition and method of treating a traumatic injury by improving immunologic response and reducing a hypermetabolic resting metabolic state associated with those suffering from the traumatic injury such as a substantial burn, trauma, major surgery and the like and more particularly to those suffering from a substantial thermal burn injury to the skin or other areas through the administration of the composition of the invention to those in need of such treatment.

The composition of the invention is a nutritionally fortified pharmaceutical composition for the treatment of a traumatic injury comprising:

an intact protein, in an amount of about 20 to 30 percent of the total energy intake;

carbohydrate, in an amount of about 65-70 percent of the total energy intake; and fat or lipids, a greater proportion of which do not enter the arachidonic acid pathway, such as oleic acid, yet includes a sufficient amount of linoleic acid to prevent an essential fatty acid deficiency thereof, and omega-3 fatty acids of fish oil including eicosapentaenoic acid to provide a total lipid in an amount of about 7-15 percent of the total energy intake, thereby decreasing the amount of arachidonic acid pathway metabolites formed in one suffering from a traumatic injury and reducing the hypermetabolic resting metabolic state and the depressed immune response associated with one suffering from a traumatic injury.

Preferably, the composition includes nutritionally necessary vitamins and minerals.

The intact protein may be derived from the group consisting of lactalbumin, egg albumen or whey, and the like. A property common to the protein which may be used in the invention is that it have a high biologic value. That is, that the protein is better at supporting animal growth relative a protein with a low biologic value. The intact protein supplies about 20 to 30 percent of the total energy intake of the patient. Where the total energy intake of protein is greater than 30 percent, adverse effects, such as weight loss, appear. The optimum range appears to be about 20-25 percent of the total energy intake. The preferred intact protein is whey protein.

The carbohydrate is selected from the group consisting of intact carbohydrates, complex glucose polymers and disaccharides. The intact form of a carbohydrate is derived from cereals, pureed vegetables and complex starches. The intact carbohydrate may be partially hydralized to yield complex glucose polymers. The preferred carbohydrate is a complex glucose polymers such as POLYCOSE (Ross Laboratories, Columbus, Ohio) or SUMACAL (Chesebrough-Ponds).

The elemental forms of either carbohydrate and/or protein require less digestive capability than the intact macronutrients such as the intact protein or intact carbohydrate. However, the increased number of particles with the elemental formulations will increase osmolality which may potentially increase certain adverse effects such a diarrhea.

Preferably the composition includes arginine in the amount of about 1-3 percent of the total energy intake to enhance healing of a wound or break in the continuity of soft parts of body structure caused by the traumatic injury and to improve immune response. The most preferred amount is 2 percent of the total energy intake.

The amount of intact protein, carbohydrate and lipid is present in the composition within their respective specified range of total energy intake.

The composition may further include the amino acids: cysteine and histidine in an amount sufficient to establish and maintain normal plasma levels. Plasma levels of these amino acids have been found to be subnormal in patients suffering from a substantial burn injury.

The composition of the invention preferably includes nutritionally necessary expedients such as vitamins and minerals. Commercial preparations such as NUTRISOURCE Vitamins and NUTRISOURCE minerals by Sandoz are readily available.

The lipid provides 7-15 percent of the total calories and always includes a limited amount of linoleic acid sufficient to prevent an essential fatty acid deficiency thereof. The lipid also always includes omega-3 fatty acids of fish oil including eicosapentaenoic acid in an amount sufficient to attenuate or reduce a hypermetabolic resting metabolic state resulting from a traumatic injury, especially a substantial burn injury. Any remaining lipid which is needed to attain the 7-15 percent of the total calories is provided by lipids which do not enter the arachidonic acid pathway.

The remaining lipid of the inventive composition may be provided by long-chain fatty acids which are present in butterfat and vegetable oils. The vegetable oils include peanut oil, olive oil, safflower oil and sunflower oil and the like. The amount of linoleic acid in vegetable oils must be considered when determining the amount to be used in the composition without providing any excess over that required to prevent a deficiency thereof. The lipid may be further provided by medium chain triglycerides (MCT). When medium chain triglycerides are used an effective amount of essential fatty acids must be either included in the composition of the invention or otherwise provided to the patient in order to prevent essential fatty acid deficiency. Preferably, the omega-3 fatty acids including eicosapentaenoic acid are provided by fish oil. Omega-3 fatty acids C20:5 eicosapentaenoic acid and C22:6 docosahexaenoic acid are typical of fish oil. More specifically, the omega-3 fatty acids of fish oil include eicosapentaenoic acid, docosahexaenoic aid, docosapentaenoic acid and linolenic acid. The exact percentages of fatty acids in fish oil may vary between species.

The fatty acid components of fish oil include:
C14:0 (Myristic) 7.01%; C14:1—0.36%;
C15:0—0.63%; C15:1 and C15:0 (BR)—0.14%;
C16:0—17.03%; C16:1 (palmitoleic)—8.68%;
C17:0—2.24%; C17:1 and C17:0 (BR)—1.11%;
C18:0 (Stearic)—4.79%; C18:1 (oleic)—12.75%;
C18:2 (linoleic)—omega 6—1.79%; 18:3 (linolenic-)—omega 3—0.46%;
C20:0 (arachidic)—2.19%;
C20:1—1.57%; C20:5 (eicosapentaenoic)—omega-3—17.43%;
C22:1—0.73%;
C22:5 (docosapentaenoic)—omega-3—3.20%;
C22:6 (docosahexaenoic)—omega-3—16.84%.

See Sanders, T. A. B. and Roshanai, F., Clinical Science, Vol. 64 pp. 91-99, 1983 the disclosure of which is incorporated herein as if fully set forth herein for a discussion of fish oil. Cod liver oil also contains omega-3 fatty acids. However, because of the amount necessary to provide sufficient omega-3 fatty acids, toxicity from high levels of Vitamin A may arise. Therefore, the use of cod liver oil as a source of omega-3 fatty acids is less desirable. Further, any arachidonic acid present in any oil would may have to be considered relative the amount of linoleic acid since arachidonic acid is derived from linoleic acid and enters the arachidonic acid pathway. A mechanical mixture of the omega-3 fatty acids as present in fish oil would be expected to perform substantially as fish oil which naturally includes omega-3 fatty acids.

In a preferred embodiment, the lipid consists of a mixture of substantially equal amounts of nonprotein calories provided by fish oil which contains eicosapentaenoic acid and by safflower oil, where the lipid supplies about 15 percent of the nonprotein calories.

Safflower oil, commercially available as MICROLIPID (Organon Inc., West Orange, N.J.) contains about 74 percent linoleic acid. Fish oil and marine oils contain high levels of eicosapentaenoic acid. MaxEPA (R.P. Scherer Corp., Clearwater, Fl.) is a commercially available fish oil which contains about 18 percent eicosapentaenoic acid.

A more specific embodiment of the invention embraces a nutritionally fortified pharmaceutical enteral composition for the treatment of a traumatic injury comprising:

whey protein, in an amount of about 20-25 percent of the total energy intake;

arginine, in an amount of about 2 percent of the total energy intake to enhance wound healing;

complex glucose polymers, in an amount of about 65 percent of the total energy intake;

a lipid in an amount of about 12 percent of the total energy intake, comprising a mixture of substantially equal amounts of nonprotein calories provided by vegetable oil with a sufficient amount of linoleic acid to prevent an essential fatty acid deficiency thereof and fish oil in an amount sufficient to reduce the hypermetabolic resting metabolic state associated with one suffering from a traumatic injury; and nutritionally necessary vitamins and minerals.

Preferably, the composition further includes cysteine and histidine which each supply about one-half percent (0.5 percent) of the total energy intake of the patient to provide normal plasma levels.

Preferably the mixture of substantially equal amounts of nonprotein calories provided by safflower oil and fish oil, in an amount of about 12 percent of the total energy intake of the patient.

Preferably the arginine is supplied in the amount of about 1-3 of the total energy intake to enhance healing of a wound or break in the continuity of soft parts of body structure caused by the traumatic injury and improve immune response.

Enteral support is the preferred route of nutrient delivery. However, diarrhea often accompanies this route, especially continuous nasogastric hyperalimentation. Diarrhea disturbs fluid and electrolyte balance and worsens nutritional status. Tube feeding hyperosmolality and serum albumin levels are the suggested key causative factors in tube feeding-induced diarrhea via hypertonicity mechanisms.

In another embodiment of the invention, the low fat composition provides for the treatment of a traumatic injury by decreasing the risk of diarrhea when combined with Vitamin A and is enterally administered preferably within 48 hours after the inflection of the traumatic injury and most preferably within 24 hours. The enteral composition comprises:

an intact protein, in an amount of about 20 to 30 percent of the total energy intake;

carbohydrate, in an amount of about 65 to 70 percent of the total energy intake;

Vitamin A in an amount sufficient to substantially decrease the risk of diarrhea;

lipids, in an amount of about 7 to 15 percent of the total energy intake comprising an amount of linoleic acid sufficient to prevent an essential fatty acid deficiency thereof and eicosapentaenoic acid in an amount sufficient to reduce a hypermetabolic resting metabolic state associated with one suffering from a traumatic injury, especially a substantial burn injury.

The enteral composition which substantially decreases the risk of diarrhea usually associated with tube feeding formulas, includes an amount of Vitamin A sufficient to provide 5,000 I.U. per day for enteral administration to a child from 9 months through 3 years of age. For a patient older than 3 years, including an adult, the enteral composition includes an amount of Vitamin A greater than about 10,000 I.U. per day. Possible toxic effects of large doses of Vitamin A exist, however amounts up to 50,000 I.U. daily are considered safe for up to 8 months. Preferably the enteral composition utilizes whey for the intact protein, a mixture of substantially equal amounts of nonprotein calories provided by fish oil and by safflower oil, where the lipid supplies about 15 percent of the nonprotein calories for the lipid and includes arginine, supplying about 2 percent of the total energy intake, and cysteine and histidine each supplying about one-half percent of the total energy intake.

The invention may also be incorporated into a method of treating a traumatic injury, especially where the traumatic injury is a substantial thermal burn injury to the skin and involved areas. The traumatic injury is treated by administering an amount of a composition comprising omega-3 fatty acids of fish oil including eicosapentaenoic acid sufficient to reduce or inhibit a hypermetabolic resting metabolic state associated with those suffering from a traumatic injury such as a substantial burn, trauma, major surgery and the like and especially to those suffering from a substantial thermal burn injury to the skin or other areas.

Preferably, the method includes administering to one in need of such treatment omega-3 fatty acids of fish oil including eicosapentaenoic acid in an amount sufficient to inhibit the onset of a hypermetabolic response associated with traumatic injury and improve immune response as soon as possible after the injury to maximize the benefit of inhibiting or attenuating the hypermetabolic response and to lessen the risk of infection by improving immunologic response. Increases in resting energy expenditure and catabolic hormones are reduced when enteral feeding is implemented immediately after a burn. Conversely, when enteral restriction is imposed while passively waiting for post-traumatic ileus to resolve, a noticeable hypermetabolic syndrome follows. Typically, metabolic rate is normal on the first two days following burn injury and then climbs dramatically over the course of several weeks. However, when burns exceed about 50 percent total body surface area or in some cases of sepsis, metabolic rate plateaus or may even decrease. Evidence appears to support a chronic elevation of catecholamines which act as the dominant stimulus of the hypermetabolic response to burns. Increased plasma catecholamines and high urinary catecholamine excretion have been correlated with burn size and metabolic rate. Enteral feeding should begin within 48 hours postburn and preferably within 24 hours postburn and most preferably within 6 hours postburn. The suppression of hypermetabolic response is evidenced by decreased resting energy expenditure, positive nitrogen balance and normal serum concentration of the catabolic hormones. Other benefits from early GI feeding include the ability to immediately satisfy nutritional requirements along with promoting bowel mucosal integrity and improved tube feeding tolerance. Preferably, the enteral composition is administered by utilizing a nasogastric tube connected to low Gomco suction while simultaneously enterally feeding via a nasoduodenal tube within 24 hours postburn.

Preferably the composition includes the omega-3 fatty acids of fish oil eicosapentaenoic and docosahexaenoic acids. Most preferably the composition includes fish oil containing the omega-3 fatty acids eicosapentaenoic acid and docosahexaenoic acid.

More specifically, the method of treating burn injuries further includes restricting the intake of linoleic acid such that only the amount necessary to meet the essential fatty acid requirement is met thereby minimizing the amount of arachidonic acid pathway metabolites associated with linoleic acid. The amount of linoleic acid necessary to prevent a deficiency is about 3-4 percent of the total energy intake.

Preferably, the method of treating a traumatic injury by enterally administering to one in need of such treatment a composition of the invention which comprises:

an intact protein, in an amount of about 20 to 30 percent of the total energy intake;

arginine, in an amount sufficient to enhance wound healing and improve immune response;

carbohydrate, in an amount of about 65-70 percent of the total energy intake; and fat or lipids, comprising a greater proportion of lipids which do not enter the arachidonic acid pathway, such as oleic acid, yet including a sufficient amount of linoleic acid to prevent an essential fatty acid deficiency thereof, and omega-3 fatty acids of fish oil including eicosapentaenoic acid where the total lipid is supplied in an amount of about 7-15 percent of the total energy intake, thereby decreasing the amount of arachidonic acid pathway metabolites formed in one traumatically injured and reducing the hypermetabolic resting metabolic state associated with one suffering from a traumatic injury. Preferably, the composition may include nutritionally necessary vitamins and minerals.

A more specific embodiment of the method of treating a traumatic injury by enterally administering to one in need of such treatment a composition of the invention which comprises:

whey protein, in an amount of about 20 to 25 percent of the total energy intake;

arginine, in an amount sufficient to enhance wound healing and improve immune response;

complex glucose polymers, in an amount of about 65-70 percent of the total energy intake; and a lipid, comprising a mixture of substantially equal amounts of nonprotein calories provided by vegetable oil having a sufficient amount of linoleic acid to prevent an essential fatty acid deficiency thereof and fish oil which contains eicosapentaenoic acid in an amount sufficient to decrease the amount of arachidonic acid pathway metabolites formed in one suffering from a traumatic injury and to reduce the hypermetabolic resting metabolic state associated with one suffering from a traumatic injury.

Preferably, the method includes administering the composition of the invention containing nutritionally necessary vitamins and minerals.

Preferably, the method includes enterally administering the composition further containing cysteine and histidine which each supply about one-half percent of the total energy intake of the patient.

Preferably, the method includes enterally administering the composition where the mixture of substantially equal amounts of nonprotein calories provided by safflower oil and fish oil is supplied in an amount of about 7-15 percent of the total energy intake of the patient.

Preferably, the method includes enterally administering the composition further containing arginine in an amount of 1-3 percent of the total energy intake to enhance healing of a wound or break in the continuity of soft parts of body structure caused by the traumatic injury and improve immune response.

The preferred method of administering the composition of the invention includes the continuous enteral administration to one in need of such treatment. That is, the continuous enteral administration is preferred over the intermittent enteral administration of the composition of the invention. The most preferred method includes enterally administering the composition of the invention to one in need as soon as possible after the infliction of the traumatic injury.

The composition of the invention is intended to be the sole source of dietary energy or total energy intake (protein, carbohydrate and lipid) for the time the patient is unable to take food by mouth. Typically, a patient who has suffered traumatic injury, especially a traumatic burn injury, is not able take food by mouth for a period of time following the injury.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DISCUSSION

The present invention discloses a nutritionally fortified pharmaceutical composition and method which is suitable for using in patients suffering from traumatic injuries, such as burn injuries which initiate a hypermetabolic state.

Figure 1:
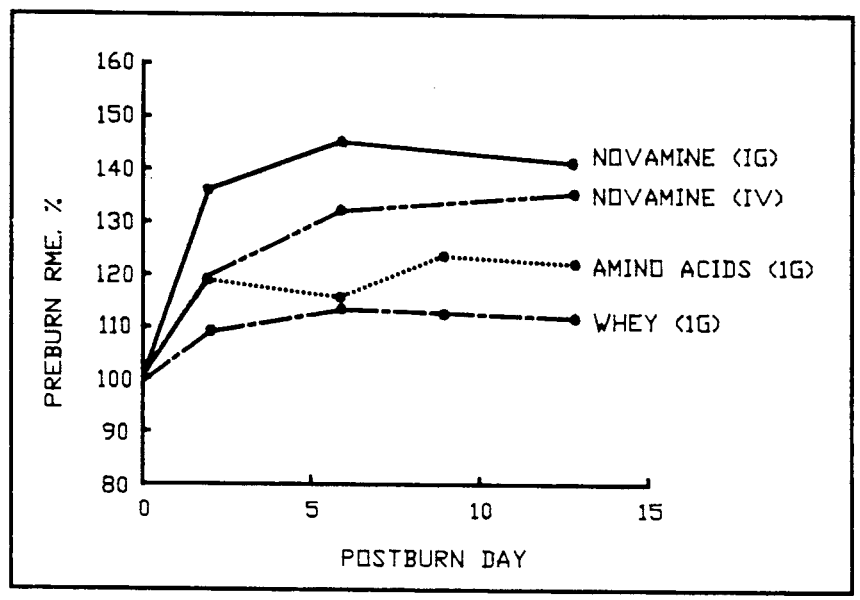
FIG. 1 is a comparison of the metabolic rates of different groups of animals receiving similar diets, except for the amino acid composition, by continuous administration.

FIG. 1 is a comparison of the resting metabolic expenditure (RME) of different groups of animals continuously receiving similar diets (isocaloric, isontrogenous and isovolemic) except for the amino acid composition. NOVAMINE, a commercially available amino acid composition was administered intragastrically (IG) and intravenously (IV). An Amino Acid group was administered intragastrically (IG) and comprised crystalline amino acids in the same amounts found in whey protein. As illustrated at FIG. 1, all groups demonstrated an increase in RME, however, the group receiving whey protein clearly demonstrated whey protein's ability to keep the resting metabolism nearest to the preburn RME. The crystalline amino acids present in the same amounts as found in whey protein also restricted the metabolic rate increase, but not to the extent of the intact whey protein.

Figure 2:
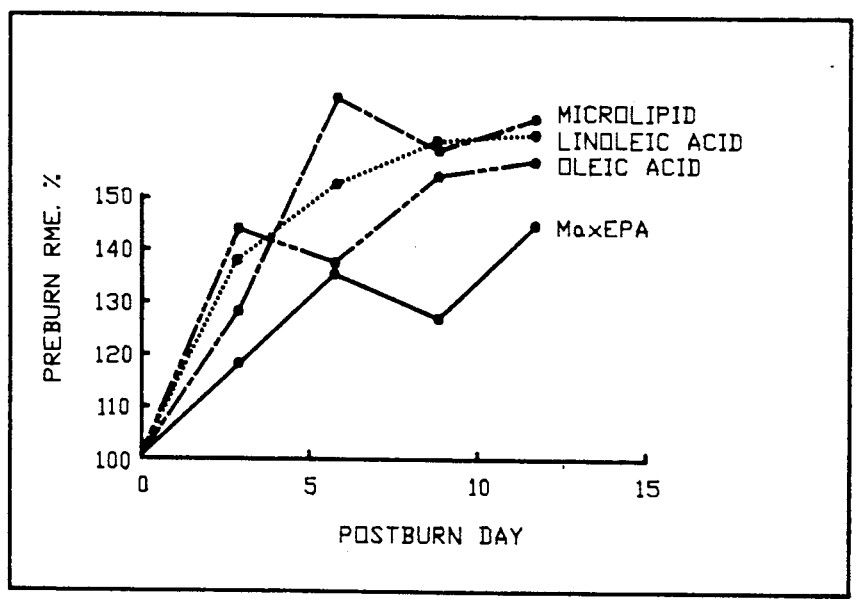
FIG. 2 is a comparison of resting metabolic rates of burned animals receiving different types of lipids in their diets.

FIG. 2 is a comparison of resting metabolic rates of burned animals receiving similar diets but different types of lipids: MICROLIPID (74 percent linoleic acid and 15 percent oleic acid), linoleic acid, oleic acid and MaxEPA. The lipid comprised 10 percent of the total energy intake. As clearly indicated the hypermetabolic response was inhibited for the group of animals which received MaxEPA (fish oil). It is theorized that linoleic acid and other omega-6 fatty acids enter the arachidonic acid pathway thereby increasing the production of certain metabolites (dienoic prostaglandins) which appear to have adverse effects on the healing process of one suffering from a traumatic injury, such as a substantial burn. Among the metabolites are the dienoic prostaglandins $PGE_2$, $PGI_2$ and $TXA_2$. FIG. 2 illustrates that arachidonic acid pathway metabolites contribute to the adverse effects of lipids following burn injury, as evidenced by the differences in inhibition of the hypermetabolic state by the compared lipids.

Figure 3:
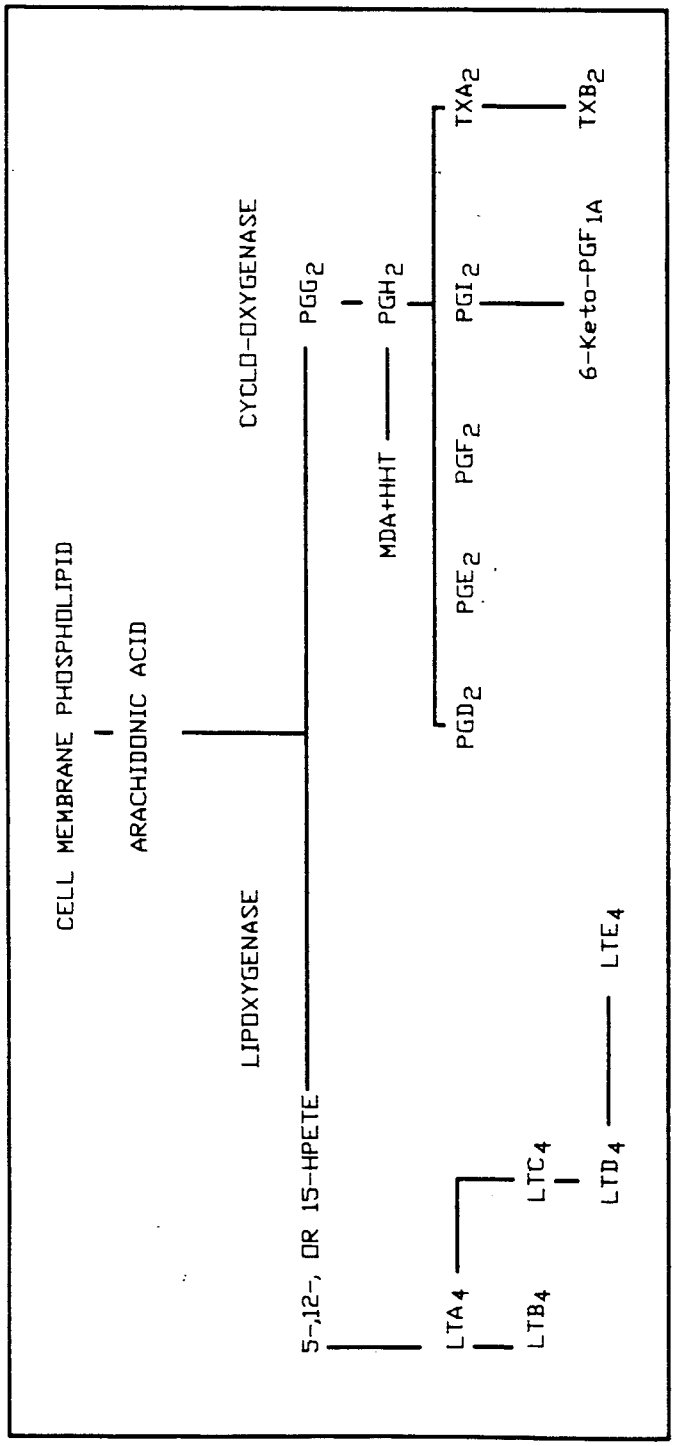
FIG. 3 is a simplified display of the metabolites of arachidonic acid.

FIG. 3 is a simplified display of the metabolites of arachidonic acid. HPETE indicates 5(S)-hydroperoxy-6,8,14-eicosatetraenoic; LT=leukotriene; PG=prostaglandin; MDA=malondialdehyde; HHt=(12S)-12-hydroxy-5,8,10-hepatodecatrienoic and TX=thromboxane. It appears that the balance between $TXA_2$ and $PGI_2$ takes part in the regulation of vascular responses, platelet aggregation and thrombosis. $PGE_2$ by itself is a vasodialtory prostaglandin that may cause edema formation. However, $PGE_2$ in combination with bradykinin, histamine, and/or degradation products of a complement pathway present a synergistic potentiation in the formation of edema. More importantly, $PGE_2$ is a potent depressant of immune response and has feedback mechanisms that inhibit the activities of interleukin-1 and interleukin-2 as well as stimulating the development and activity of suppressor T cells. Accordingly, the biological effects manifested by the metabolites of the arachidonic acid pathway explains the adverse effects manifested by their presence.

Figure 4:
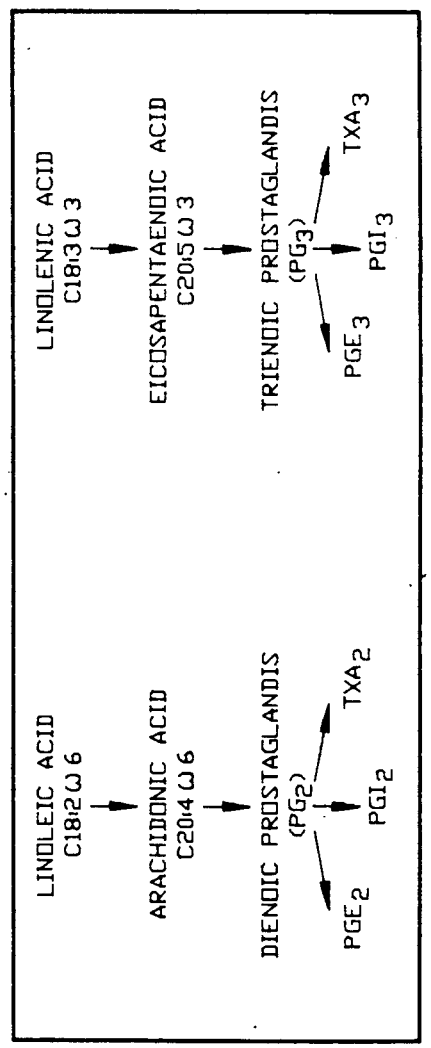
FIG. 4 is a comparison of the dienoic and trienoic prostaglandin pathways.

FIG. 4 is a comparison of the dienoic and trienoic prostaglandin pathways. TX=thromboxane. The trienoid prostaglandin metabolites $PGI_3$, $PGE_3$ and $TXA_3$ are equivalent to the major metabolites $PGE_2$, $PGI_2$ and $TXA_2$ of the dienoid prostaglandins. However, $PGE_3$ and $TXA_3$ lack potency when compared with their dienoid counterparts and block the action of $PGE_2$ and $TXA_2$. Thus, regulation of dietary lipids by controlling the intake of omega-6 fatty acids controls the synthesis of dienoic prostaglandins and therefor the adverse effects associated therewith.

A more through discussion is set forth in: Alexander, J. Wesley, Nutrition and Infection, Arch. Surg., Volume 21, pp. 966-972 (August 1986); Alexander, J. Wesley, The Importance of Lipid Type in the Diet after Burn Injury, Ann. Surg., Volume 204, No. 1, pp. 1-8 (July 1986) and, Gottschlich, Michele and Alexander, J. Wesley, Fat Kinetics and Recommended Dietary Intake in Burns, J. Parenteral and Enteral Nutrition, Volume 11, No. 1, pp. 80-85 (1987), and Trocki O., Saito H., Gonce S. J., Heyd T. J., Alexander J. W., Effects of Dietary Lipids on Postburn Metabolic and Immune Response, JPEN 10:50, 1986 each of which is incorporated herein by reference as if fully set forth herein.

Fish oil which is rich in trienoic prostaglandin precursors exerts beneficial effects on gastrointestinal, immunologic and inflammatory response when compared to fat from vegetable oils which are largely composed of dienoic prostaglandin precursors in the management of burns.

In one embodiment of the invention an enteral composition utilized as its protein source, 87 percent whey protein with 9 percent arginine, 2 percent cysteine and 2 percent histidine (100 percent of the protein) at 57 grams per liter. The protein source supplied about 20 percent of the total energy intake required by the patient. The carbohydrate source was maltodextrin which supplied about 85 percent of the nonprotein calories (about 68 percent of the total energy intake) and was added at a rate of 164 grams per liter. The lipid source consisted of fish oil and safflower oil providing 15 percent of the nonprotein calories (about 12 percent of the total calories) with substantially equal amounts of nonprotein calories provided by the fish oil (MaxEPA), which contained eicosapentaenoic acid and docosahexaenoic acid, and by the safflower oil. The fish oil-safflower mixture was added at a rate of 13 grams per liter. The fish oil-safflower oil mixture included 4.8 grams linoleic acid per liter. The composition of the invention supplies about 1000 kcalories per liter and had an osmolality of 549 mOsm/Kg water.

An enteral composition of the invention was prepared as set forth below:

| Modular Tube Feeding-Shriners Burns Institute | | | | | |
|---|---|---|---|---|---|
| Ingredients | Amount | CHO | PRO | FAT | KCAL |
| Sterile Water | 750 ml | | | | |
| MaxEPA (fish oil) | 6 ml | 0 | 0 | 6 | 54 |
| MICROLIPID | 9 ml | 0 | 0 | 4.4 | 39 |
| PROMIX | 62 g | 3.3 | 50 | 2.6 | 236 |
| SUMACAL | 149 g | 142 | 0 | 0 | 568 |
| Arginine HCL | 5 g | 0 | 5 | 0 | 20 |
| Histidine | 1 g | 0 | 1 | 0 | 4 |
| Cysteine | 1 g | 0 | 1 | 0 | 4 |
| NUTRISOURCE Minerals | 24 g | 6 | 0 | 0 | 24 |
| NUTRISOURCE Vitamins | 20 g | 18 | 0 | 0 | 72 |
| Vitamin A (50,000 units/ml) | 0.1 ml | 0 | 0 | 0 | 0 |
| TOTAL | | 163.3 | 57 | 13 | 1021 |

The sterile water was measured and poured into a blender such as a Waring blender. The MaxEPA (R. P. Scherer Corporation) (fish oil) was measured using a pipette and/or graduated cylinder. The MICROLIPID (Chesebrough-Ponds) preparation was vigorously shaken and measured utilizing a pipette. Both of these liquids are added to the blender. PROMIX (Navaco) was weighed out and added to the blender. SUMACAL (Chesebrough-Ponds) was weighed and add to liquids in blender. The Arginine HCL, Histidine and Cysteine were individually weighed and added to the liquids in the blender. Twenty four grams of NUTRISOURCE (Sandoz) Minerals and 20 grams of NUTRISOURCE (Sandoz) Vitamins were added to the liquids in the blender. Vitamin A was measured and added to the liquids in the blender. All ingredients were mixed in the blender at low speed for about 30 seconds taking caution not to over mix. The foam was allowed to settle. To check proper recipe level, the liquid was poured into a 2000 ml flask and more sterile water was added if necessary to bring up to the correct 1000 ml level. The formula provided about 1000 Kcal. The formula was transferred into a brown bottle and refrigerated. After 24 hours any remaining formula is discarded. To prepare an enteral composition of the invention which decreases the risk of diarrhea, an amount of Vitamin A is added to the composition as described above.

| CALCULATION FORMULA FOR 1000 ml | |
|---|---|
| Kcal needs | = 1000 |
| Protein needs (20% of Kcal) | = 200 Kcal or 50 g protein |
| Arginine needs (2% of Kcal) | = 20 Kcal or 5 g arginine |
| Histidine needs (0.5% of Kcal) | = 5 Kcal or 1 g |
| Cysteine needs (0.5% of Kcal) | = 5 Kcal or 1 g |
| 1000 Kcal | |
| −230 Kcal (arginine + histidine + cysteine + Promix) | |
| 770 Kcal from nonprotein sources | |
| Total fat | = 15% of nonprotein calories |
| | = .15 × 770 = 115 Kcal or 13 g fat |
| Fat from Maxepa | = 7% of nonprotein calories |
| | = .07 × 770 = 54 Kcal or 6 g Maxepa |
| | = 6 ml |
| Fat from Microlipid | = 8% of nonprotein calories |
| | = 13 − (2.6 + 6) |
| | = 4.4 g of Microlipid |
| | = 9 ml |
| Carbohydrate | = 85% of nonprotein calories |
| | = .85 × 770 = 655 Kcal or 163 g carbohydrates |
| 230 Kcal (protein) + 115 Kcal (fat) + 655 Kcal (carbohydrate) | = 1000 Kcal |

The composition may further include about 220 mg/day zinc sulfate where the occurrence of a suboptimal serum level is encountered in a traumatically injured patient. The composition may further include about 1 gm of vitamin C per day.

Diarrhea is a frequent problem in the use of enterally administered enteral compositions. In an effort to determine the cause, a study was conducted. Diarrhea was defined as greater than 4 liquid bowel movements per day or a large (greater than 200 g) liquid stool. Of the 20 patients studied, 6 (30%) developed diarrhea. Stool cultures were negative for pathogenic organisms. The mean total body surface area burn of those who developed diarrhea was 55 percent (range 12-89%) whereas those without diarrhea had a mean burn size of 43 percent (range 28-71%) (not significant). Results demonstrated a significant relationship between dietary lipid content and diarrhea. Implementation of tube feeding within 48 hours postburn was associated with a decreased incidence of diarrhea. The risk of diarrhea was most closely associated with inadequate Vitamin A intake. Surprisingly, tube feeding osmolality, systemic antibiotics, or hypoalbuminemia did not have an adverse effect on intestinal absorption. Various enteral feeding products were compared. This study demonstrated a highly significant effect of the lowfat enteral composition of the invention augmented with vitamin A, as set forth above, in decreasing the risk/incidence of diarrhea associated with enteral feeding.

Numerous methods and formulas exist for determining the daily caloric needs of traumatically injured patients. Formulas such as the Curreri formula has been found workable in initially projecting energy needs in burn patients: (25 kcal×kg body weight)+(40 kcal×percent burn). While helpful in estimating peak energy needs, the Curreri formula leads to overfeeding as the patient progresses. The failure of the Curreri formula and other conventional formulas, is that they do not account for many effectors of energy balance over time. The object of any formula must be to provide adequate calories for positive nitrogen balance and satisfactory maintenance of body weight without overfeeding. To attain this object, energy expenditure is ascertained by measuring oxygen consumption of the patient by means known in the art. However, other energy requiring activities such as physical therapy, hydrotherapy and dressing changes can elevate energy needs and must be considered. Therefore, providing nutritional intake equivalent to 1.3 times the measured energy expenditure at rest is associated with conditions of positive nitrogen balance and satisfactory maintenance of body weight in the majority of burn patients.

The composition may be prepared in a dry form, with the lipid in an accompanying vial, for subsequent reconstitution by the addition of water and lipid. Such methods are well known in the art. Also, the composition may be prepared as needed or prepared as a ready-to-use composition by methods well known in the art.

The present disclosure includes that contained in the appended claims as well a that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed:

1. A method of treating a traumatic injury which manifests a resting hypermetabolic state by administrating to one suffering from such an injury, a composition comprising an amount of omega-3 fatty acids of fish oil sufficient to reduce the resting hypermetabolic state associated with the traumatic injury.

2. A method of treating a traumatic injury which manifests a resting hypermetabolic state by administrating to one suffering from such an injury, a composition comprising
    an amount of omega-3 fatty acids of fish oil sufficient to reduce the resting hypermetabolic state associated with the traumatic injury; and
    an amount of linoleic acid limited to only the amount necessary to meet the essential fatty acid requirement of linoleic acid thereby reducing the amount of arachidonic acid pathway metabolites associated with the metabolism of linoleic acid.

3. A method of treating a traumatic injury by reducing a hypermetabolic resting metabolic state associated with the traumatic injury by enterally administering to one in need of such treatment an effective amount of a composition comprising:
    an intact protein, in an amount of about 20 to 30 percent of the total energy intake;
    carbohydrate, in an amount of about 65 to 70 percent of the total energy intake;
    lipids, in an amount of about 7 to 15 percent of the total energy intake, comprising an amount of linoleic acid sufficient only to prevent an essential fatty acid deficiency thereof thereby reducing the amount of arachidonic acid pathway metabolites in the traumatically injured patient, and omega-3 fatty acids of fish oil including eicosapentaenoic acid in amount sufficient to reduce a hypermetabolic resting metabolic state associated with one suffering from a traumatic injury.

4. The method of claim 1 wherein the method further includes continuous enteral administration of the composition to one in need of such treatment.

5. The method of claim 3 wherein the traumatic injury is a substantial thermal burn injury to the skin.

6. The method of claim 4 further administering the composition as soon as possible within 24 hours after the infliction of the traumatic injury.

7. The method of claim 3 wherein the composition includes arginine in an amount sufficient to enhance healing of a wound or break in the continuity of soft parts of body structure caused by the traumatic injury.

8. The method of claim 3 wherein the omega-3 fatty acids are provided by fish oil.

9. A method of treating a traumatic injury by reducing a hypermetabolic resting metabolic state associated with the traumatic injury by enterally administering to one suffering from a traumatic injury an effective amount of a composition comprising:
    whey protein, in an amount of about 20 to 25 percent of the total energy intake;
    arginine in an amount sufficient to enhance healing of a wound or break in the continuity of soft parts of body structure caused by the traumatic injury;
    carbohydrate, in an amount of about 65 to 70 percent of the total energy intake where the carbohydrate is complex glucose polymers;
    lipids, where the lipid supplies about 12 percent of the total energy intake and is provided by a mixture of substantially equal amounts of nonprotein calories provided by fish oil which comprises omega-3 fatty acids and by vegetable oil with a sufficient amount of linoleic acid to prevent an essential fatty acid deficiency thereof, thereby reducing the amount of arachidonic acid pathway metabolites formed in the traumatically injured patient and reducing a hypermetabolic resting metabolic state associated with one suffering from a traumatic injury.

10. The method of claim 9 wherein the traumatic injury is a substantial thermal burn injury to the skin.

* * * * *